United States Patent [19]

Berg et al.

[11] Patent Number: 5,455,282

[45] Date of Patent: Oct. 3, 1995

[54] PROCESS OF REGENERATING SULFONIC ACID CATION EXCHANGE RESINS WITH A MERCAPTOETHYLAMINE OR THIAZOLIDINE

[75] Inventors: Klaus Berg; Georg Malamet; Franz Backes, all of Krefeld; Alfred Eitel, Dormagen; Claus Wulff, Krefeld, all of Germany

[73] Assignee: Bayer Aktiengesellschaft, Leverkusen, Germany

[21] Appl. No.: 380,207

[22] Filed: Jan. 30, 1995

Related U.S. Application Data

[62] Division of Ser. No. 220,523, Mar. 31, 1994, abandoned.

[30] Foreign Application Priority Data

Apr. 13, 1993 [DE] Germany ............... 43 12 038.5

[51] Int. Cl.$^6$ ............... B01J 38/50; B01J 39/04; B01J 39/18
[52] U.S. Cl. ............... 521/26; 521/32; 521/33; 568/722; 568/723; 568/727; 568/728

[58] Field of Search ............... 521/26; 568/727, 568/728

[56] References Cited

U.S. PATENT DOCUMENTS

| | | | |
|---|---|---|---|
| 3,394,089 | 7/1968 | McNutt | 521/33 |
| 4,045,379 | 8/1977 | Kwantes | 521/33 |
| 4,308,404 | 12/1981 | Kwantes | 568/727 |
| 4,369,293 | 1/1983 | Heydenreich et al. | |
| 4,396,728 | 8/1983 | Faler | |
| 5,075,511 | 12/1991 | Li | |
| 5,302,774 | 4/1994 | Berg | 568/727 |
| 5,315,042 | 5/1994 | Cipullo | 568/727 |

FOREIGN PATENT DOCUMENTS

| | | |
|---|---|---|
| 023325 | 4/1981 | European Pat. Off. |
| 049411 | 4/1982 | European Pat. Off. |
| 268318 | 5/1988 | European Pat. Off. |

*Primary Examiner*—Fred Zitomer
*Attorney, Agent, or Firm*—Connolly & Hutz

[57] ABSTRACT

The invention relates to repeatedly regeneratable ion exchanger resins with a thin covering of alkyl-SH groups.

3 Claims, No Drawings

PROCESS OF REGENERATING SULFONIC ACID CATION EXCHANGE RESINS WITH A MERCAPTOETHYLAMINE OR THIAZOLIDINE

This application is a divisional of application Ser. No. 08/220,523 filed on Mar. 31, 1994 now abandoned.

This invention relates to repeatedly regeneratable ion exchanger resins with a thin covering of alkyl SH groups.

The condensation of phenols and carbonyl compounds to form bisphenols is known. Various catalysts have already been used for this reaction, including for example hydrochloric acid (U.S. Pat. Nos. 2,182,308 and 2,191,831), boron trifluoride (Chemical Abstracts 58, 3338 c), perchloric acid (Chemical Abstracts 60, 1626 h), Benzene sulfonic acid (Chemical Abstracts 59, 511 h) and various cation exchanger resins (for example GB-PS 842,209, 849,565 and 883,391). The addition of S-containing compounds to the catalyst is also known. For example, the use of thioglycolic acid and 3-mercaptopropionic acid is known from U.S. Pat. Nos. 2,468,982 and 2,623,908; the addition of thiophenols is known from U.S. Pat. Nos. 2,359,242; the addition of alkyl mercaptans is known from U.S. Pat. Nos. 2,775,620 and the addition of hydrogen sulfide is known from Chemical Abstracts 58, 1403 e.

U.S. Pat. No. 3,394,089 describes a process for the production of bisphenol from acetone and phenol using a catalyst containing sulfonic acid groups in which 5 to 25 mol-% of the sulfonic acid groups are covered with mercaptoamines. The fixing of co-catalytically active compounds to the resin matrix a) improves the selectivity and reactivity of the bisphenol synthesis and b) avoids contamination of the end product with sulfur compounds.

DE-A 3 619 450 describes a process in which covering of the ion exchanger with mercaptoalkyl amines is carried out in phenol-moist phase. This is said to give the resin a particularly long life. The resin has a covering of sulfonic acid groups of 30 to 100 mol-% (based on sulfonic acid groups).

However, it has been found that the life of ion exchanger systems modified with OH groups is shorter by a factor of 10 by comparison with unmodified ion exchanger systems. This eliminates the advantages of the modified system because lives as short as these are not economically acceptable.

If, in the initial covering of the ion exchanger system, 5 mol-% and more of the —SO₃H groups have been covered, the original conversion activity is no longer achieved after deactivation and re-covering. A third covering after re-covering no longer achieves the original conversion activity and is no longer worthwhile in view of the resulting considerable reduction in the reactivity of the ion exchanger. Accordingly, the ion exchanger has to be expensively regenerated or disposed of at considerable cost. Accordingly, the useful lives are very short.

It has now been found that an ion exchanger with a covering of <5 mol-% can be regenerated after deactivation by re-covering with species containing alkyl —SH groups.

Accordingly, the present invention relates to macroporous or gel-like sulfonic acid ion exchanger resins having degrees of crosslinking of 1 to 20%, in which 1 to 3 mol-% of the sulfonic acid groups have been covered with species containing alkyl —SH groups.

This covering may be carried out by ionic or covalent bonding. Mercaptoethyl amines or precursors thereof (thiazolidines) as described in U.S. Pat. No. 3,394,089 and in DE-A 36 19 450 are mentioned as examples of the species.

Gel-like or macroporous sulfonic acid ion exchangers with degrees of crosslinking of 1 to 20% may be used as the matrix. The ionically fixed units may be applied by methods of the type described in U.S. Pat. No. 3,394,089 or in DE-A 36 19 450.

The coverage of the ion exchanger with alkyl —SH units according to the invention amounts to between 1 and 3 mol-% and has the following advantages:

a) the reactivity and selectivity of such catalyst systems are only negligibly lower than those of systems with higher coverages;

b) the life of a catalyst resin covered with 1 to 3 mol-% alkyl-SH units, based on SO₃H groups, is comparable with that of a catalyst resin with higher coverage (≧5 mol-%);

c) the lightly covered resin can be repeatedly regenerated (up to 5 times) by re-covering with 1 to 3 mol-% SH-alkyl units (based on SO₃H groups) without any significant reduction in its activity. Its useful life is thus increased by a factor of 3 to 5 in relation to the systems with higher degrees of coverage.

According to the invention, mercaptoethyl amines corresponding to formula (I):

$$HS-CH_2CH_2-NR^1R^2 \qquad (I)$$

in which

R¹ and R² independently of one another represent (H) or C₁₋₄ alkyl, or thiazolidines corresponding to formula (II)

in which

R¹ is hydrogen (H) or C₁₋₄ alkyl, are used as species containing alkyl-SH groups.

Mixtures of compounds (I) and (II) may be used.

The production of bisphenol A, for example, with the ion exchanger covered in accordance with the invention may be carried out continuously or discontinuously. The reaction temperature in the production of the bisphenols is in the range from 40° to 120° C. and preferably above the solidification point of the components involved. The reaction mixture obtained after the reaction of phenolic and carbonyl compound is worked up by known methods, such as crystallization, distillation, etc.

The ion exchangers according to the invention may be produced by covering sulfonated polystyrene resins with mercaptoalkyl amines corresponding to formula (I) and/or thiazolidines corresponding to formula (II).

In addition, deactivated ion exchangers, in which 1 to 3 mol-% of the sulfonic acid groups have already been covered one or more times with alkyl-SH units, may be regenerated by re-covering with alkyl-SH units (1 to 3 mol-%, based on the sulfonic acid groups). Resins which originally contained up to 25 mol-% alkyl-SH units (based on sulfonic acid units) may also be covered with resins, albeit with reduced efficiency.

EXAMPLES

Example 1

Production of the modified ion exchanger resin (commercial polystyrene, sulfonated, with a degree of crosslinking of 1 to 20%):

The water-moist ion exchanger (approx. 80% by weight water moisture) with a total capacity of 0.75 mval/ml as supplied is first washed with distilled water. The resin is then dried for 24 hours at 90° to 100° C. in a water jet pump vacuum, so that its water content falls to less than 1% by weight.

The residual water is distilled off in an azeotropic mixture with toluene, after which the toluene still adhering to the ion exchanger resin is distilled off in a water jet pump vacuum at 95° C.

120 g of the ion exchanger resin thus pretreated are taken up in 1.128 g phenol in a stirred apparatus and swollen for 24 h at 65° C. in the absence of moisture. The quantity of mercaptoethylamine required for a certain coverage in mol-% of Examples 2 to 10 is then added with stirring.

Example 2

An ion exchanger resin in which 5 mol-% of the sulfonic acid groups were covered with cysteamine ($NH_2$—$CH_2$—$CH_2$—$SH$) was prepared by the process described in Example 1. A standard test was then carried out with the resin:

1.128 g phenol and 58 g acetone were added to 250 g phenol-moist ion exchanger, followed by stirring in a stirred apparatus for 4 hours at 65° C. The conversion and selectivity of the reaction are then determined by gas chromatography (standard mixture).

Conversion: 95.5%
Selectivity: 94.0%

Example 3

The test described in Example 2 is repeated with a resin in which 2.8 mol-% of the sulfonic acid groups have been covered with mercaptoethylamine.

Conversion: 94.9%
Selectivity: 93.8%

Example 4

An ion exchanger originally covered with 5 mol-% mercaptoethylamine, but deactivated in the meantime, was re-covered with 5 mol-% mercaptoethylamine and subjected to the standard test described in Example 2:

Conversion: 75.3%
Selectivity: 93.7%

Example 5

An ion exchanger originally covered with 2.8 mol-% mercaptoethylamine, deactivated, subsequently re-covered with 2.8 mol-% and then deactivated again was re-covered with 2.8 mol-% mercaptoethylamine and subjected to a standard test:

Conversion: 90.1%
Selectivity: 93.1%

Example 6 (Comparison)

An ion exchanger originally covered with 5 mol-% mercaptoethylamine, deactivated, subsequently re-covered with 5 mol-% and then deactivated again was re-covered with 5 mol-% mercaptoethylamine and subjected to a standard test:

Conversion: 48.7%
Selectivity: 90.4%

Example 7 (Comparison)

An ion exchanger originally covered with 5 mol-% mercaptoethylamine, but deactivated in the meantime, was subjected to the standard test described in Example 1.

Conversion: 29.2%
Selectivity: 80.3%

We claim:

1. A process for regenerating a deactivated, ion-exchange resin bed containing sulfonic acid groups one or more times, which comprises contacting the deactivated resin bed with a mercaptoethylamine or a thiazolidine to cover the resin with 1–3 mol % of alkyl-SH groups, based on sulfonic acid groups.

2. The process of claim 1, wherein the resin is a macroporous or gel form sulfonic acid ion exchange resin which is 1–20% crosslinked.

3. The process of claim 1, wherein the resin bed is regenerated between 1 and 5 times.

* * * * *